(12) United States Patent
Richard et al.

(10) Patent No.: US 10,265,050 B2
(45) Date of Patent: Apr. 23, 2019

(54) DUAL DISPLAY PRESENTATION APPARATUS FOR PORTABLE MEDICAL ULTRASOUND SCANNING SYSTEMS

(71) Applicant: Sonoscanner SARL, Paris (FR)

(72) Inventors: Bruno Richard, Paris (FR); Etienne Richard, Paris (FR); Pierre-Adrien Nadal, Paris (FR)

(73) Assignee: SONOSCANNER SARL, Paris (FR)

( * ) Notice: Subject to any disclaimer, the term of this patent is extended or adjusted under 35 U.S.C. 154(b) by 317 days.

(21) Appl. No.: 14/872,637

(22) Filed: Oct. 1, 2015

(65) Prior Publication Data
US 2017/0095230 A1 Apr. 6, 2017

(51) Int. Cl.
*A61B 8/00* (2006.01)

(52) U.S. Cl.
CPC .......... *A61B 8/4427* (2013.01); *A61B 8/4483* (2013.01); *A61B 8/463* (2013.01); *A61B 8/465* (2013.01); *A61B 8/467* (2013.01); *A61B 8/56* (2013.01); *A61B 8/4411* (2013.01); *A61B 8/4416* (2013.01)

(58) Field of Classification Search
CPC .................................................... A61B 8/4427
See application file for complete search history.

(56) References Cited

U.S. PATENT DOCUMENTS

| | | | | |
|---|---|---|---|---|
| 8,535,227 B2* | 9/2013 | Halmann | ................. | A61B 8/14 600/407 |
| 2005/0228281 A1* | 10/2005 | Nefos | ....................... | A61B 8/08 600/446 |
| 2011/0043434 A1* | 2/2011 | Roncalez | ............ | G06F 3/04847 345/3.1 |
| 2012/0133600 A1* | 5/2012 | Marshall | ............... | G06F 19/321 345/173 |
| 2014/0362096 A1* | 12/2014 | Otsuka | .................. | G06F 3/1423 345/531 |

* cited by examiner

*Primary Examiner* — Tse W Chen
*Assistant Examiner* — Jason M Ip
(74) *Attorney, Agent, or Firm* — Greer, Burns & Crain, Ltd.

(57) ABSTRACT

A portable ultrasound scanning system comprising a hand-held housing, ultrasound electronics of a complete ultrasound scanning system, including a beamformer and an image processing unit, contained within the hand-held housing. A first display comprises a touchscreen on the hand-held housing with a user input interface, at least partially presented on the first display. A probe containing a plurality of piezoelectric transducers is controlled by the ultrasound electronics and is connected to the housing via a cable. The ultrasound electronics are configured to receive signals from the probe and to convert those signals and provide converted signals to the first display to display a scanned ultrasound image on the first display. A second, larger, display is located remote from the housing. A connection arrangement is configured to selectively connect the second display to the ultrasound electronics, and automatically upon such connection, display the scanned image on the second display.

16 Claims, 3 Drawing Sheets

DUAL DISPLAY PRESENTATION APPARATUS FOR PORTABLE MEDICAL ULTRASOUND SCANNING SYSTEMS

FIELD OF THE DISCLOSURE

The present disclosure generally relates to portable medical ultrasound scanners having interactive displays, and in particular relates to a portable medical ultrasound scanning system with a dual display presentation apparatus.

BACKGROUND OF THE INVENTION

Most conventional full-sized ultrasound scanning systems have a video display and a user interface directly attached or connected to each other for facilitating an intimate examination of scanned images by an operator, such as an ultrasound technician or a physician. Typically such full-sized systems are desk or cart supported and are movable only by pushing a relatively large cart or wheeled system into position relative to the patient, or having the patient position themselves relative to the ultrasound system.

As known in the art, the conventional full-sized ultrasound scanning systems are typically equipped with large ultrasound scanners with relatively large corresponding screens, such that high-resolution images are generated and displayed on the large screen. The ultrasound scanning system and the screens are connected to each other by wired connections and are also directly wired to the domestic or commercial power supply system for the building, such as 110 volt, 60 cycle current (in the US) and 220 volt, 50 cycle current (in Europe). A separate, large keyboard is also provided with the conventional ultrasound scanning system for inputting commands and a trackball, mouse, trackpad or other pointing device for moving a cursor on the screen of the display.

The full-sized ultrasound scanning systems generally are provided with a number of input sockets for receiving cable connectors for different ultrasound probes that may be used for scanning different portions of a human body or other objects of interest. The probes provided for the full-sized systems are provided with a large number, such as 128 or 256, of transducers to provide a high resolution scan image. Generally, each transducer is connected by a separate channel or wire to the ultrasound electronics for conversion into the display image. Thus, the cables connecting the probes to the ultrasound electronics housing contain hundreds of shielded wires for the transducer signals, as well as wires for electrical power and control of the transducers.

Although these full-sized components of the conventional ultrasound scanning system provide high quality scanned images, manual mobilization of such conventional systems is difficult and their use is limited generally to dedicated locations in a health care facility. Further, these full sized systems require direct connection to an electrical power supply in that the ultrasound electronics and the displays consume a significant amount of power. The costs for such full-sized ultrasound units are also relatively high.

There have been developed and commercialized smaller, more portable scanning systems, such as based on units that have a size similar to lap top computers (portable) or even hand-held tablets (ultraportable), however these portable and ultra-portable units have suffered from some drawbacks. Although these units allow the ultrasound scanning of a patient to occur in locations that are not dedicated for ultrasound scanning, including at the hospital bedside or other locations, the image quality on the correspondingly smaller screens of these portable systems is reduced, due to the small size of the screen, and also due to the reduced number of transducers provided in probes used in these portable systems. Many of these portable systems operate on battery power carried in the hand-held unit, allowing for limited power available for the scanner probes, and leading to a reduced number of transducers in the probes. This reduced number of transducers results in a reduced resolution of the image typically displayed on the small screen of the portable unit.

The relative small screens of the portable and ultraportable ultrasound scanning systems make it difficult to the medical personnel to clearly see the images provided by the scanning system, and to accurately measure structures detected by the scanning system. Also, it is often desirable to show the scanned images to the patients or other observers while the scanning is occurring. With the portable and ultraportable systems, the small size of the screen makes this difficult and the orientation of the small screen towards the medical personnel operator, for controlling the imaging of the scanner, also detracts from allowing the patient and other observers to clearly see the scanned images.

It would be advantageous to provide a portable or ultraportable ultrasound scanning system that generates a high quality image on a screen, and also that would provide a high quality image on a large screen visible to the patient, as well as to the medical personnel operating the ultrasound equipment.

SUMMARY OF THE INVENTION

Advantages are achieved by the present portable medical ultrasound scanning system which includes a capability to display the scanned image on a second relatively larger display screen. An important aspect of the present portable medical ultrasound scanning system is that the scanned images are displayed either on a touchscreen associated with the present scanning system or on a larger separate, additional display device.

An important aspect of the present medical ultrasound scanning system is that the present system is highly portable and substantially small in size without altering an image resolution quality of the scanned images. As a result, high resolution images are displayed on the relatively small touchscreen as if the same images were shown on the full size screen of the large conventional ultrasound scanner. Thus, the scanned images are freely transferrable between the touchscreen of the portable scanning system and the larger display device without having to compensate or adjust for resolution differences between the touchscreen and the larger display device.

In one embodiment, a portable ultrasound scanning system is provided which comprises a hand-held housing, ultrasound electronics of a complete ultrasound scanning system, including a beamformer and an image processing unit, contained within the hand-held housing, a first display comprising a touchscreen mounted on the hand-held housing, a user input interface, at least a part of which is presented on the first display, and being configured to receive inputs from the user via the touch screen and to transmit those inputs to the ultrasound electronics, a memory unit carried in the hand-held housing and electrically connected to the central processing unit, a probe containing a plurality of piezoelectric transducers controlled by the ultrasound electronics and connected to the hand-held housing via a probe cable, a power supply contained within the hand-held unit and being electrically connected to the ultrasound electronics and the probe, the ultrasound electronics being configured to receive signals from the probe via the probe cable and to convert those signals and provide converted signals to the first display to display a scanned ultrasound image on the first display, a second display, larger than the first display, located remote from the hand-held housing, and a connection arrangement configured to selectively connect the second display to the ultrasound electronics, and automatically upon such connection, display of the scanned image is presented on the second display.

In an embodiment, the connection arrangement comprises a switch operated by the user input interface and a wireless transmission component for wirelessly transmitting image signals to the second display.

In an embodiment, the connection arrangement comprises a display cable connected at one end to the second display, and a socket on the hand-held housing configured to receive a second end of the display cable.

In an embodiment, the connection arrangement further comprises a sensor to detect the presence of the display cable, and to send a signal to the central processing unit to send the signals for the scanned image to the display cable when the presence of the display cable is detected.

In an embodiment, the user interface comprises the touch screen and at least one depressible button.

In an embodiment, the hand-held housing is sized to as to be carried by an adult in a single hand.

In an embodiment, the piezoelectric transducers comprise high density transducers.

In an embodiment, the power supply comprises a battery.

In an embodiment, the probe is detachable and replaceable with respect to the hand-held housing.

In an embodiment, the second display has a display area more than 4 times greater than a display area of the first display.

In an embodiment, the second display has a power supply independent of the power supply located in the hand-held housing.

In an embodiment, the first display includes a display area for the scanned image and a display area for the user interface.

In an embodiment, the connection arrangement is configured to remove the scanned image from the first display when the second display is connected to the ultrasound electronics and to enlarge the display area for the user interface on the first display.

In an embodiment, the user interface on the first display comprises a keyboard when the second display is connected to the ultrasound electronics.

The foregoing and other aspects and features of the disclosure will become apparent to those of reasonable skill in the art from the following detailed description, as considered in conjunction with the accompanying drawings.

DETAILED DESCRIPTION OF THE PREFERRED EMBODIMENTS

Figure 1:
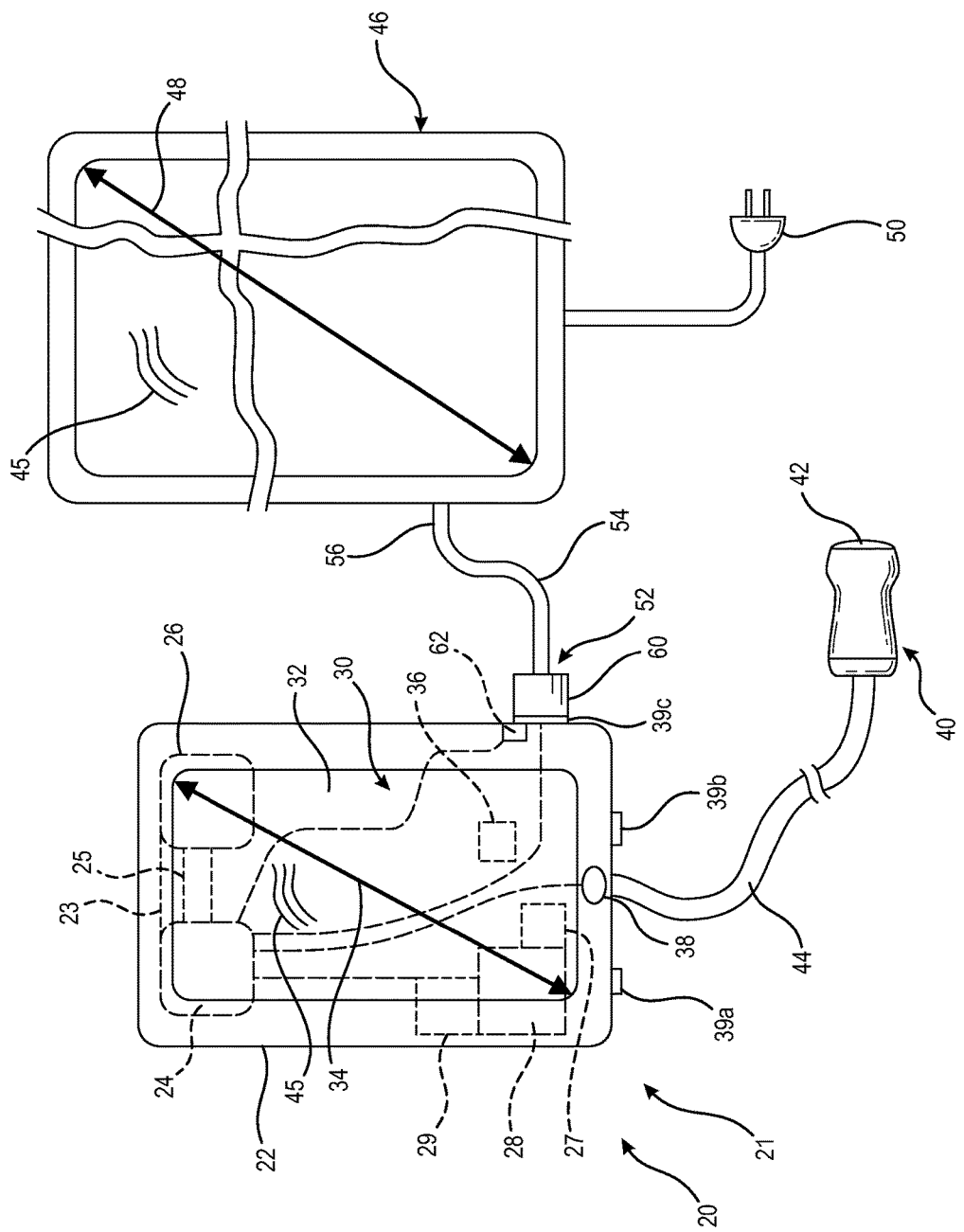
FIG. 1 illustrates an exemplary portable medical ultrasound scanning system in accordance with an embodiment of the present disclosure.
Figure 2:
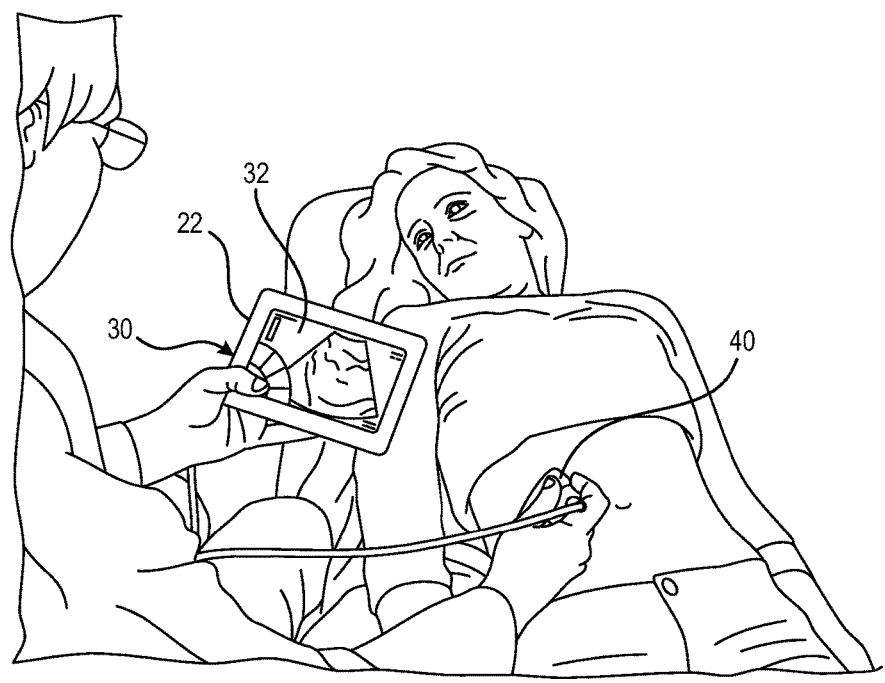
FIG. 2 illustrates an exemplary practice of the present medical ultrasound scanning system of FIG. 1, utilizing a portable device having a virtual user interface, and an interchangeable probe.

Preferred embodiments of the present disclosure are described below by way of example only, with reference to the accompanying drawings. Further, the following description is merely exemplary in nature and is in no way intended to limit the disclosure, its application, or uses.

As used herein, the term "module," or "unit" may refer to, be part of, or include a programmable integrated circuit, an electronic circuit, a processor (shared, dedicated, or group) and/or memory (shared, dedicated, or group) that execute one or more software or firmware programs, a combinational logic circuit, and/or other suitable components that provide the described functionality.

Although children modules residing in their respective parent modules are shown, the broad teachings of the present system can be implemented in a variety of forms. Thus, while this disclosure includes particular examples and arrangements of the modules, the scope of the present system should not be so limited since other modifications will become apparent to the skilled practitioner.

Exemplary embodiments herein below are directed primarily to medical ultrasound scanning systems. However, the present system can be implemented for other types of ultrasound scanning products or services. Thus, the terms "patient" and "tissue" are used to refer to the objects being scanned, and should be understood to refer also to other types of objects.

Referring now to FIGS. 1-3 and 5, a portable ultrasound scanning system 20 is illustrated which includes a hand-held housing 22. The housing 22 is preferably sized to be carried in one hand of an adult, and preferably does not exceed a size of 30 cm by 30 cm (12 inches by 12 inches) with a thickness not exceeding 5 cm (2 inches). The weight of the housing 22, with all internal components discussed below, preferably does not exceed 1 kilogram (2.2 pounds). In a preferred embodiment, the hand-held housing 22 has a size of approximately 12.7 cm (5 inches) by 17.8 cm (7 inches), with a thickness of about 2 cm (0.9 inches), which allows the housing to fit and easily be carried in a standard size pocket on a medical personnel lab coat. The hand-held housing 22 preferably has a weight of about 600 gm (1.3 pounds) or less. Other sized housings 22 may be used with the present invention, but in a preferred embodiment, the housing has a weight of less than 1000 gm (2.2 pounds), more preferably a weight of less than 800 gm (1.8 pounds) and most preferably, a weight of no more than 600 gm (1.3 pounds).

The hand-held housing 22 contains ultrasound electronics 21 of a complete ultrasound scanner, including a beamformer 23, a central processing unit with a control module 24, a computing unit 25, a memory unit 26, an image processing unit 27, a power supply 28, and an optional wireless transmitter and receiver 29, all electrically interconnected. The ultrasound electronics 21 are configured to contain and operate conventional hardware, firmware and/or software for operating an ultrasound scanner in a known manner and displaying the scanned image on a display, as discussed below. The power supply 28 preferably comprises a rechargeable battery, such as a lithium polymer battery capable of providing several hours of operation for the ultrasound scanning system 20. Other types of power supplies including line power (alternating current) or other types of power storage devices, including different battery types, may be used as well. It is contemplated that the line power may be used in conjunction with a power converter, such as an AC-DC adapter.

A first display 30, comprising a touchscreen 32, is mounted on the hand-held housing 22. Preferably the display 30 has a display area 34 of a size in the range of 10.2 cm (4 inches) to 38.1 cm (15 inches) as measured on the diagonal of the rectangular display area. In a preferred embodiment, the display 30 has a display area 34 of a size of about 17.8 cm (7 inches) as measured on the diagonal.

A user input interface 36 is provided, at least a part of which is presented on the first display 30. The user input interface 36 is configured to receive inputs from the user via the touchscreen 32 and to transmit those inputs to the central processing unit 24.

A variety of different user input interfaces 36 may be utilized within the scope of the present invention. In a preferred embodiment, the user input interface is presented on at least a portion of the touchscreen 32 and can be operated by the user with one or more of the fingers of the hand holding the hand-held housing 22. The user interface may comprise several selectable areas of information or control that may be alternately selectably displayed on the touch screen. A particular type of user interface is described in more details in co-pending U.S. patent application Ser. No. 14/872,616, the disclosures of which are incorporated herein by reference. The user input interface 36 may include one or more buttons or switches 38 by means of which the user may activate the portable ultrasound scanning system 20, or provide other inputs to the central processing unit 24 of the ultrasound electronics 21.

Various ports and connectors may be provided in the housing 22, such as a connector 39a for a power supply, a USB port 39b, an HDMI port 39c, as well as ports for other types of connectors.

A probe 40 is provided which contains a plurality of piezoelectric transducers 42 controlled by the ultrasound electronics 21. Preferably high density or fine pitch multi-element electronic probes (e.g., 128-256 transducer elements for linear, convex and endocavitary probes or 64 transducer elements for phased array probes) are used as the probe, such that a high quality image can be produced by the ultrasound scanning system 20.

The probe 40 is connected to the hand-held housing 22 via a probe cable 44. The probe 40 may be permanently attached to the hand-held housing 22 if the portable ultrasound scanning system 20 is dedicated to a single type of scanning, or the probe 40 may be detachable and a different probe 40 attached to the hand-held housing 22 to permit different types of scanning to be performed by a single portable ultrasound scanning system 20. A particular type of detaching and reattaching arrangement for the probe 40 that may be utilized is disclosed and described in co-pending U.S. patent application Ser. No. 14/872,655, the disclosures of which are incorporated herein by reference.

The ultrasound electronics 21 are configured to send and receive signals from the probe 40 via the probe cable 44 and to convert the signals from the probe and provide converted signals to the first display 30 to display a scanned ultrasound image 45 on at least a portion of the first display 30 in a manner known in the art. The display of the scanned ultrasound image 45 may occupy a portion of the area of the first display 30, with a remaining portion of the area being available for display of user interface display icons and interactive icons.

A second display 46, preferably larger than the first display 30, is located remote from the hand-held housing 22. The second display 46 preferably has a display area 48 that is considerably larger than the display area 34 of the first display 30, for example, at least 4 times larger. In a preferred embodiment, the second display 46 comprises a flat video screen display with a rectangular display area 48 of at least 61 cm (24 inches) as measured on the diagonal. The second display 46 preferably has its own power supply 50, independent of the power supply 28 in the hand-held housing 22.

A connection arrangement 52 is configured to selectively connect the second display 46 to the ultrasound electronics 21, and automatically upon such connection, the scanned image is presented on the second display 46. The connection arrangement 52 may comprise a display cable 54 connected at one end 56 to the second display 46, and a socket, such as HDMI port 39c on the hand-held housing 22 configured to receive a second end 60 of the display cable 54. As an example, the display cable 54 may be an HDMI cable, with appropriate connectors at the end 60 of the cable and at the hand-held housing 22.

The connection arrangement 52 may further comprise a sensor 62, such as a switch or connector terminal or a software detection algorithm, to detect the presence of the display cable 54 at the socket 39c, and to send a signal to the ultrasound electronics 21 to send the signals for the scanned image 45 to the display cable 54 (and second display 46) when the presence of the display cable 54 is detected. It is also possible for the user input interface 36 to have an input area that may be touched to cause the signals for the scanned image 45 to be sent to the display cable 54 and second display 46 rather than, or in addition to, the first display 30.

The connection arrangement 52 may also comprise a switch operated by the user input interface and a wireless transmission component 29 in the ultrasound electronics 21 for wirelessly transmitting image signals to the second display.

All relevant information can be stored in a central database in the memory unit 26 which comprises a machine readable data storage medium carrying computer programs, for retrieval by the ultrasound electronics 21.

During use, the operator holds the hand-held housing 22 having the virtual user input interface 36, and manipulates the probe 40 on the skin or in a body cavity of a patient. The scanned image 45 appears on the first display 30, so long as the second display 46 is not connected.

An important aspect of the present ultrasound scanning system 20 is that at least one external, remote second display 46 is electrically coupled to the hand-held housing 22, and is oriented to the patient, such that both the user and patient can simultaneously view scanned images 45 in a larger screen format of the second display 46 during the diagnostic imaging process. As discussed above, the second display 46 can be directly (wired) connected to the hand-held housing 22 for displaying the images 45 associated with a scanned structure or object via the display cable 54. Alternatively, the second display 46 can be indirectly (wireless) connected to the ultrasound electronics 21 in the hand-held housing via suitable wireless communication technologies, such as Wi-Fi, Bluetooth.

It is contemplated that the scanned images 45 are freely transferrable between the first display 30 and the second display 46 without having to compensate or adjust for any resolution differences between the first display 30 and the second display 46. For example, one or more scanned images 45 are automatically transmitted to the second display 46 when the connection between the second display 46 and the ultrasound electronics is established.

Figure 5:
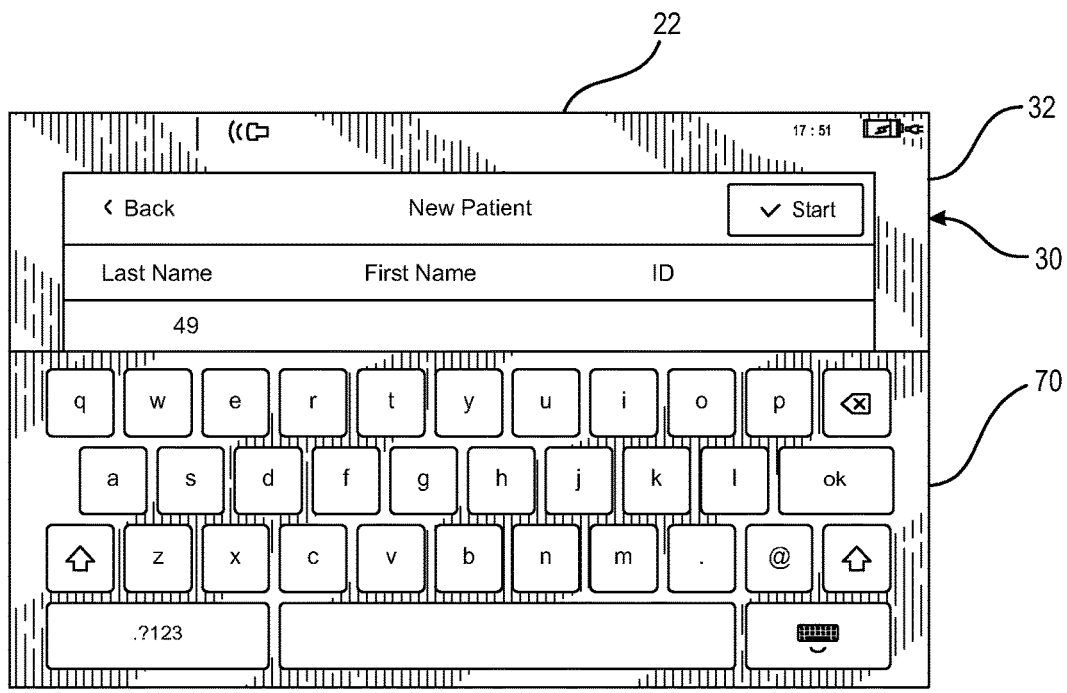
FIG. 5 illustrates an exemplary keyboard displayed on the portable device of FIG. 2.

In a preferred mode of operation, the scanned images 45 are then no longer displayed on the first display 30, and instead, the entire display area of the first display 30 then shows only the user input interface, which may include a keyboard (FIG. 5), a virtual pointing device and other user input or interface display areas on the touchscreen 32. As an example only, FIG. 5 shows a separate, large keyboard 70 being displayed on the first display 30 for inputting new patient information.

Figure 3:
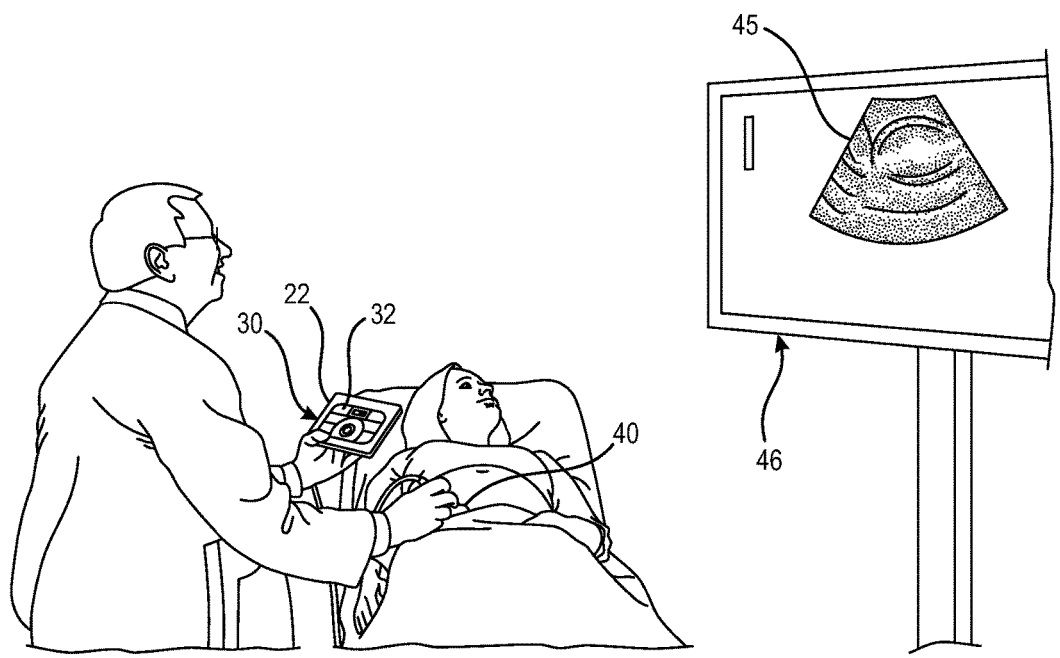
FIG. 3 illustrates another exemplary practice of the present medical ultrasound scanning system of FIG. 1, featuring the portable device and a separate, additional display device.
Figure 4:
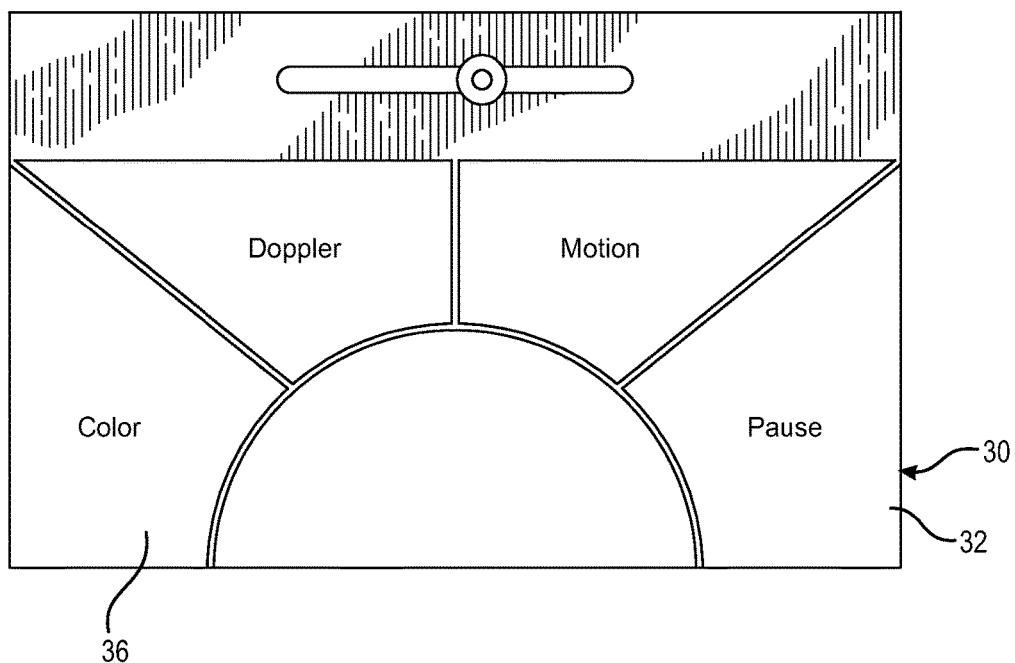
FIG. 4 illustrates an exemplary screen of the portable device of FIG. 2, transitioning the virtual user interface into another configuration.

Referring now to FIGS. 3 and 4, an aspect of the interface mode is that the touchscreen 32 automatically transforms into an interactive input device. Specifically, when the interface mode is activated, the scanned image 45 is automatically transferred from the first display 30 to the second display 46, and is illustrated only on the larger screen of the second display. Then, the touchscreen 32 displays only the user input interface 36 without the scanned image. It is contemplated that the user input interface 36 is automatically visually enlarged, or more components displayed, when the interface mode is activated for utilizing additional space created by elimination of the scanned image 45 on the touchscreen 32.

While at least one exemplary embodiment of the present invention has been shown and described, it should be understood that modifications, substitutions and alternatives may be apparent to one of ordinary skill in the art and can be made without departing from the scope of the invention described herein. This application is intended to cover any adaptations or variations of the specific embodiments discussed herein. In addition, in this application, the terms "comprise" or "comprising" do not exclude other elements or steps, and the terms "a" or "one" do not exclude a plural number. Furthermore, characteristics or steps which have been described with reference to one of the above exemplary embodiments may also be used in combination with other characteristics or steps of other exemplary embodiments described above.

What is claimed is:

1. A portable ultrasound scanning system comprising:
   a hand-held housing sized to be carried in one hand of an adult user by being no larger than 12.7 cm by 17.8 cm and no more than 2 cm thick, and weighing no more than 600 grams,
   ultrasound electronics of an ultrasound scanning system, including a beamformer, a central processing unit, a computing unit, a memory unit, a power supply and an image processing unit, contained within the hand-held housing,
   a first display comprising a touchscreen mounted on the hand-held housing having a size of at least 17.8 cm as measured on a diagonal of a rectangular display area,
   a user input interface, at least a part of which is presented on the first touchscreen display in an area arranged to be accessed and operated by the user with one or more fingers of the hand of the user holding the hand-held housing, and being configured to receive inputs from the user via the touchscreen and to transmit those inputs to the ultrasound electronics,
   a probe containing at least 64 piezoelectric transducers controlled by the ultrasound electronics and connected to the hand-held housing via a detachable probe cable,
   a power supply contained within the hand-held unit and being electrically connected to the ultrasound electronics and the probe,
     the ultrasound electronics being configured to receive signals from the probe via the probe cable and to convert those signals and provide converted signals to the first display to display a scanned ultrasound image on the first display,
   a second, optional display, larger than the first display, located remote from the hand-held housing, and
   a connection arrangement configured to selectively connect the second, optional display to the ultrasound electronics, and automatically upon such connection, exclusive display of the scanned image is presented on the second display and only the user input interface, including a keyboard and a virtual pointing device, being presented on the first display,
   wherein the connection arrangement comprises a display cable connected at one end to the second display, and a socket on the hand-held housing configured to receive a second end of the display cable, and
   wherein the connection arrangement further comprises a sensor to detect the presence of the display cable, and to send a signal to the central processing unit to send the signals for the scanned image to the display cable when the presence of the display cable is detected.

2. The portable ultrasound scanning system according to claim 1, wherein the user interface comprises at least one depressible button.

3. The portable ultrasound scanning system according to claim 1, wherein the power supply comprises a battery.

4. The portable ultrasound scanning system according to claim 1, wherein the probe is replaceable with respect to the hand-held housing.

5. The portable ultrasound scanning system according to claim 1, wherein the second display has a display area more than 4 times greater than a display area of the first display.

6. The portable ultrasound scanning system according to claim 1, wherein the second display has a power supply independent of the power supply located in the hand-held housing.

7. The portable ultrasound scanning system according to claim 1, wherein the first display includes a display area for the scanned image and a display area for the user interface.

8. The portable ultrasound scanning system according to claim 7, wherein the connection arrangement is configured to enlarge the display area for the user interface on the first display when the second display is connected to the ultrasound electronics.

9. A portable ultrasound scanning system comprising:
   a hand-held housing, the hand-held housing being sized to as to be carried by an adult user in a single hand and being no larger than 12.7 cm by 17.8 cm and 2 cm thick, and weighing no more than 600 grams,
   ultrasound electronics of an ultrasound scanning system, including a beamformer, a central processing unit, a computing unit, a memory unit, a power supply and an image processing unit, contained within the hand-held housing,
   a first display comprising a touchscreen mounted on the hand-held housing having a size of at least 17.8 cm as measured on a diagonal of a rectangular display area,
   a user input interface, at least a part of which is presented in a display area on the first touchscreen display in an area arranged to be accessed and operated by the user with one or more fingers of the hand of the user holding the hand-held housing, and being configured to receive inputs from the user via the touchscreen and to transmit those inputs to the ultrasound electronics,
a probe containing at least 64 piezoelectric transducers controlled by the ultrasound electronics and connected to the hand-held housing via a probe cable,
a power supply comprising a battery contained within the hand-held unit and being electrically connected to the ultrasound electronics and the probe,
the ultrasound electronics being configured to receive signals from the probe via the probe cable and to convert those signals and provide converted signals to the first display to display a scanned ultrasound image on the first display,
the first display including a display area for the scanned image and a display area for the user interface,
a second, optional display, larger than the first display, located remote from the hand-held housing, and
a connection arrangement configured to selectively connect the second, optional display to the ultrasound electronics, and automatically upon such connection, display of the scanned image is presented on the second display, the connection arrangement being configured to remove the scanned image from the first display when the second display is connected to the ultrasound electronics and to enlarge the display area for the user interface on the first display and to present a keyboard and a virtual pointing device as part of an enlarged user interface.

10. The portable ultrasound scanning system according to claim 9, wherein the connection arrangement comprises a switch operated by the user input interface and a wireless transmission component for wirelessly transmitting image signals to the second display.

11. The portable ultrasound scanning system according to claim 9, wherein the connection arrangement comprises a display cable connected at one end to the second display, and a socket on the hand-held housing configured to receive a second end of the display cable.

12. The portable ultrasound scanning system according to claim 11, wherein the connection arrangement further comprises a sensor to detect the presence of the display cable, and to send a signal to the central processing unit to send the signals for the scanned image to the display cable when the presence of the display cable is detected.

13. The portable ultrasound scanning system according to claim 9, wherein the user interface comprises the touch screen and at least one depressible button.

14. A portable ultrasound scanning system comprising:
a hand-held housing sized to be carried by an adult user in a single hand and being no larger than 12.7 cm by 17.8 cm and 2 cm thick and weighing no more than 600 grams,
ultrasound electronics of an ultrasound scanning system, including a beamformer, a central processing unit, a computing unit, a memory unit, a power supply and an image processing unit, contained within the hand-held housing,
a first display comprising a touchscreen mounted on the hand-held housing having a size of at least 17.8 cm as measured on a diagonal of a rectangular display area,
a user input interface, at least a part of which is presented on the first touchscreen display in an area arranged to be accessed and operated by the user with one or more fingers of the hand of the user holding the hand-held housing, and being configured to receive inputs from the user via the touchscreen and to transmit those inputs to the ultrasound electronics,
a probe containing at least 64 piezoelectric transducers controlled by the ultrasound electronics and connected to the hand-held housing via a probe cable,
a power supply contained within the hand-held unit and being electrically connected to the ultrasound electronics and the probe,
the ultrasound electronics being configured to receive signals from the probe via the probe cable and to convert those signals and provide converted signals to the first display to display a scanned ultrasound image on the first display,
the first display including a display area for the scanned image and a display area for the user interface, and
a connection arrangement configured to selectively connect the ultrasound electronics to a second, remote display, and automatically upon such connection, exclusive display of the scanned image is presented on the second display and removed from the first display, the connection arrangement being configured to remove the scanned image from the first display when the second display is connected to the ultrasound electronics and to enlarge the display area for the user interface on the first display,
wherein the user interface on the first display comprises a keyboard and a virtual pointing device when the second display is connected to the ultrasound electronics.

15. The portable ultrasound scanning system according to claim 14, wherein the connection arrangement comprises a switch operated by the user input interface and a wireless transmission component for wirelessly transmitting image signals to the second display.

16. The portable ultrasound scanning system according to claim 14, wherein the connection arrangement comprises a display cable connected at one end to the second display, and a socket on the hand-held housing configured to receive a second end of the display cable and wherein the connection arrangement further comprises a sensor to detect the presence of the display cable, and to send a signal to the central processing unit to send the signals for the scanned image to the display cable when the presence of the display cable is detected.

* * * * *